(12) United States Patent
Bae et al.

(10) Patent No.: US 8,702,923 B2
(45) Date of Patent: Apr. 22, 2014

(54) METHOD AND APPARATUS FOR MEASURING SAMPLE REACTION RESULTS ON BIOSENSOR

(75) Inventors: Byeong-woo Bae, Anyang-si (KR); Sung-dong Lee, Yeocheon-si (KR); Hong-seong Suk, Anyang-si (KR); Jin-a Yoo, Anyang-si (KR)

(73) Assignee: Infopia Co., Ltd., Anyang-si (KR)

( * ) Notice: Subject to any disclaimer, the term of this patent is extended or adjusted under 35 U.S.C. 154(b) by 0 days.

(21) Appl. No.: 13/010,098

(22) Filed: Jan. 20, 2011

(65) Prior Publication Data

US 2012/0043201 A1 Feb. 23, 2012

Related U.S. Application Data

(63) Continuation of application No. 11/481,086, filed on Jul. 5, 2006, now Pat. No. 7,897,033.

(60) Provisional application No. 60/706,353, filed on Aug. 8, 2005.

(30) Foreign Application Priority Data

Apr. 11, 2006 (KR) .................. 10-2006-0032890

(51) Int. Cl.
*G01N 27/26* (2006.01)
*G01N 27/327* (2006.01)

(52) U.S. Cl.
USPC .......... 204/403.01; 204/403.15; 205/792; 205/777.5; 205/775; 205/778; 435/287.1; 422/68.1; 422/82.01

(58) Field of Classification Search
USPC .......... 204/403.01–403.15; 205/777.5, 778, 205/792; 600/345–348; 422/68.1, 82.01; 435/287.1

See application file for complete search history.

(56) References Cited

U.S. PATENT DOCUMENTS

| | | | | |
|---|---|---|---|---|
| 5,582,697 A | * | 12/1996 | Ikeda et al. | 205/777.5 |
| 5,762,770 A | | 6/1998 | Pritchard et al. | |
| 6,743,635 B2 | * | 6/2004 | Neel et al. | 436/95 |
| 6,841,052 B2 | * | 1/2005 | Musho et al. | 204/401 |
| 6,875,327 B1 | * | 4/2005 | Miyazaki et al. | 204/403.14 |
| 7,491,310 B2 | * | 2/2009 | Okuda et al. | 205/777.5 |
| 2004/0154932 A1 | * | 8/2004 | Deng et al. | 205/777.5 |
| 2006/0163086 A1 | * | 7/2006 | Bae et al. | 205/775 |

FOREIGN PATENT DOCUMENTS

| | | |
|---|---|---|
| JP | 05340915 | 12/1993 |
| KR | 1020010049234 | 6/2001 |
| KR | 1020040028437 | 4/2004 |
| WO | 03034055 A1 | 4/2003 |
| WO | WO 03034055 * | 4/2003 |

* cited by examiner

*Primary Examiner* — Jennifer Dieterle
(74) *Attorney, Agent, or Firm* — NSIP Law

(57) ABSTRACT

Disclosed is a method of measuring sample reaction results on a biosensor having a working electrode and other electrodes, including: applying voltage between the working electrode and each of the other electrodes and detecting the amount of current flowing through the working electrode to determine whether or not a sample is injected; applying voltage between the working electrode and one of the other electrodes and re-detecting the amount of current flowing through the working electrode; and acquiring and displaying a concentration value as a sample reaction result corresponding to the amount of detected current.

10 Claims, 6 Drawing Sheets

METHOD AND APPARATUS FOR MEASURING SAMPLE REACTION RESULTS ON BIOSENSOR

CROSS REFERENCE TO RELATED APPLICATIONS

This application is a continuation of U.S. patent application Ser. No. 11/481,086, filed on Jul. 5, 2006, in the United States Patent and Trademark Office, which claims the priorities of U.S. Provisional Patent Application Ser. No. 60/706,353, filed on Aug. 8, 2005, in the United States Patent and Trademark Office, and Korean Patent Application No. 2006-32890, filed on Apr. 11, 2006, in the Korean Intellectual Property Office, the disclosures of which are incorporated herein by reference.

BACKGROUND OF THE INVENTION

1. Field of the Invention

The present invention relates to a biosensor and, more particularly, to a method and apparatus for measuring sample reaction results on a biosensor.

2. Description of Related Art

A biosensor has an electrode layer including a plurality of electrodes formed on an insulative substrate by screen printing or the like, and an enzyme reaction layer consisting of hydrophilic polymer, redox enzyme and electron acceptor on the electrode layer. When a sample containing a substrate is dropped on the enzyme reaction layer of the biosensor, the enzyme reaction layer is dissolved and the substrate and the enzyme are reacted with each other, thereby oxidizing the substrate and reducing the electron acceptor. A concentration of the substrate in the sample can be obtained from a current value obtained by electrochemically oxidizing the reduced electron acceptor after completion of the enzyme reaction.

A typical example of a biosensor acquiring a quantitative value of a specific ingredient of a bio-sample in an electrochemical manner is a sensor for blood sugar measurement. FIGS. 1 and 2 illustrate the sensor for blood sugar measurement.

FIG. 1 is an exploded perspective view of a typical biosensor except a reactive layer. FIG. 2 is a longitudinal sectional view of the biosensor shown in FIG. 1.

Referring to FIG. 1, leads 102 and 104 are formed by printing a silver paste on an insulative substrate 100. A working electrode 106 is formed by printing a conductive carbon paste containing a resin binder on the substrate 100. The working electrode 106 is connected to the lead 102. An insulation layer 108 is formed by printing an insulative paste on the substrate 100. The insulation layer 108 covers the periphery of working electrode 106, such that an exposed portion of the working electrode 106 maintains a fixed area. A ring-shaped counter electrode 110 is formed by printing the conductive carbon paste containing resin binder on the substrate 100 so as to be connected to the lead 104. A reactive layer is formed on or around an electrode layer consisting of the working electrode 106 and the counter electrode 110.

The substrate 100 having the reactive layer, a cover 114 having an air hole 112, and a spacer 116 are fixed to one another as shown in FIG. 1, thereby providing a biosensor. The spacer 116 has an insert hole 118 as a path for supplying a sample solution between the substrate 100 and the cover 114. A hydrophilic polymer layer 120, a reactive layer 122 including an enzyme and an electron acceptor, and a lecithin layer 124 are formed on the substrate 100 in this order.

When a bio-sample contacts an inlet 126 in the biosensor, the bio-sample is filled in the insert hole 118 by capillarity and, at the same time, air inside the insert hole 118 is discharged through the air hole 112 formed on the cover 114.

However, there is a problem in that since the air hole 112 is located over the sensor, a measurement error may occur due to contact with the air hole 112 when the sensor is used. Meanwhile, since the reaction begins to proceed at the moment when a sample contacts a reaction layer, the sample should be quickly absorbed irrespective of its viscosity. However, since the air hole 112 is located at the rear of sample path in the biosensor, it is difficult to quickly absorb the sample.

Since the biosensor includes three electrodes, detects whether or not the sample is fully injected, and makes a measurement, the above-mentioned absorption delay causes a measurement error in the biosensor.

SUMMARY OF THE INVENTION

The present invention provides a method and apparatus for measuring sample reaction results on a biosensor having three electrodes, which can detect whether or not a sample is normally injected and correctly measure reactive materials in the sample.

According to an aspect of the present invention, there is provided a method of measuring sample reaction results on a biosensor having a working electrode and other electrodes, including: applying voltage between the working electrode and each of the other electrodes and detecting the amount of current flowing through the working electrode to determine whether or not a sample is injected; applying voltage between the working electrode and one of the other electrodes and re-detecting the amount of current flowing through the working electrode; and acquiring and displaying a concentration value as a sample reaction result corresponding to the amount of detected current.

The concentration value may be acquired from a concentration value table stored in a memory.

The concentration value may be acquired by operating a predetermined factor to the amount of re-detected current.

According to another aspect of the present invention, there is provided a method of measuring sample reaction results on a biosensor having at least a working electrode, a checking electrode, and a counter electrode, including: applying voltage between the checking electrode and the working electrode, and between the counter electrode and the working electrode, and detecting the amount of currents flowing through the working electrode, and a time interval between times when the amount of two currents is detected; determining whether or not a sample is injected by comparing the amount of detected currents and the detected time interval with predetermined threshold values; applying voltage between the working electrode and the counter electrode and re-detecting the amount of current flowing through the working electrode; and acquiring and displaying a concentration value as a sample reaction result corresponding to the amount of re-detected current.

According to another aspect of the present invention, there is provided an apparatus for measuring sample reaction results on a biosensor having a working electrode and other electrodes, including: switches connecting a plurality of electrodes of the biosensor coupled to the apparatus to a ground terminal; an amplifier connected at its one terminal to a voltage source and at another terminal to the working electrode of the biosensor to detect the amount of current flowing through the working electrode; and a microprocessor controlling the switches so that voltage can be applied between the working electrode and each of the electrodes upon coupling of a sensor strip, detecting the amount of current flowing through the working electrode to determine whether or not a sample is injected, controlling the switches so that voltage can be applied between the working electrode and any one of the electrodes, re-detecting the amount of current flowing through the working electrode, acquiring and displaying a concentration value as a sample reaction result corresponding to the amount of re-detected current on a display unit.

The microprocessor may include a memory storing concentration values as sample reaction results corresponding to the amount of re-detected current.

The microprocessor may operate the amount of re-detected current to a predetermined factor to acquire a concentration value as a sample reaction result.

The microprocessor may indicate a sample recognition error if the amount of two currents detected to determine whether or not the sample is injected, and a time interval between times when the amount of the two currents is detected fail to meet a predetermined condition.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Exemplary embodiments in accordance with the present invention will now be described in detail with reference to the accompanying drawings.

Figure 1:
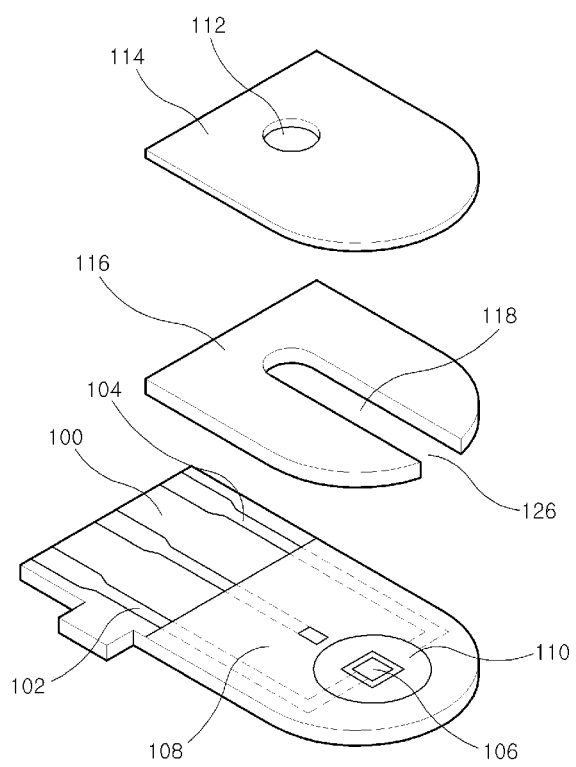
FIG. 1 is an exploded perspective view of a typical biosensor except a reactive layer.
Figure 2:
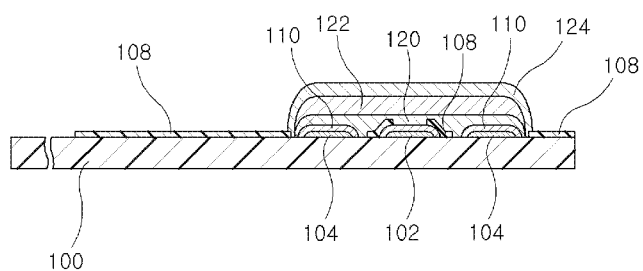
FIG. 2 is a longitudinal sectional view of the biosensor shown in FIG. 1.
Figure 3:
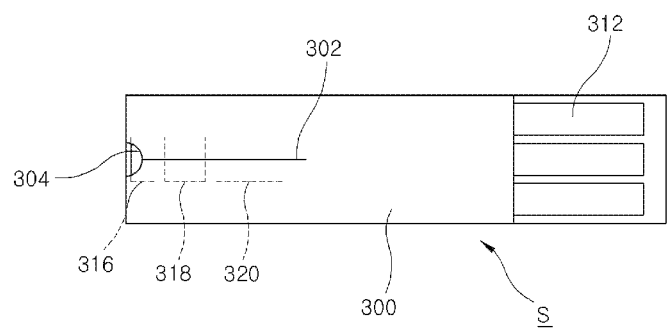
FIGS. 3 and 4 are a plan view and a rear elevation of a biosensor, respectively, which is coupled with an apparatus for measuring sample reaction results on the biosensor according to an embodiment of the present invention.
Figure 4:
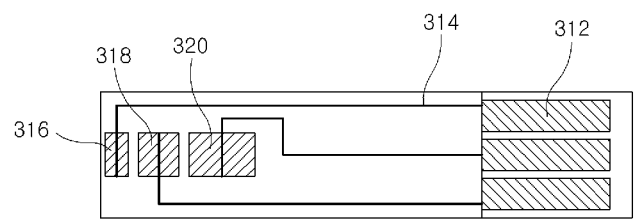

FIGS. 3 and 4 are a plan view and a rear elevation of a biosensor, respectively, which is coupled with an apparatus for measuring sample reaction results on the biosensor according to an embodiment of the present invention.

Referring to FIG. 3, lead terminals 312 corresponding to the number of electrodes are formed on an end of an insulative substrate of a biosensor S coupled with an apparatus (which is also called a biosensor measurement unit) for measuring sample reaction results according to an embodiment of the present invention. The lead terminals 312 are connected to electrodes 316, 318 and 320 that are formed on another end of the biosensor S through individual leads 314 as shown in FIG. 4.

An insert hole 302 is formed on a cover 300 of the biosensor S. A bend 304 is formed on an end of the cover 300 and bent toward the electrodes 316, 318 and 320. The insert hole 302 is extended from the bend 304 to the electrodes 316, 318 and 320. The insert hole 302 is used as an air outlet when a bio-sample is injected by capillarity.

The insulative substrate of the biosensor S is generally a polymer substrate made of non-conductive materials such as polyethylene terephtalate, polyvinyl chloride resin, or polycarbonate resin. The leads 314 and the lead terminals 312 may be formed by screen printing.

A reference numeral 316 denotes a checking electrode, 318 denotes a working electrode, and 320 denotes a counter electrode. Each of the electrodes detects the amount of current generated upon oxidation or reduction of an electron acceptor on an enzyme reaction layer.

The apparatus according to the present embodiment can detect, from the amount of current detected through the electrodes 316, 318 and 320, whether or not a sample is injected, and quantitatively measure the concentration of reactive materials in the sample.

The electrodes 316, 318 and 320 may be formed by screen printing of a conductive carbon ink. Interlayer insulation films are formed between the electrodes 316, 318 and 320. An enzyme reaction layer is formed on the electrodes, and includes an enzyme and an electron acceptor that react with the injected bio-sample. That is, different kinds of enzymes may be used according to uses of the biosensor.

In case of a sensor for blood sugar measurement, an enzyme reaction layer includes a glucose oxidase. When a blood sample is injected to the enzyme reaction layer of the sensor, blood sugar of the blood sample is oxidized by the glucose oxidase, and a blood sugar oxidase is reduced. The electron acceptor oxidizes the glucose oxidase while is itself reduced. The reduced electron acceptor loses electrons from an electrode applied with a predetermined voltage, thereby being electrochemically re-oxidized. The concentration of glucose in the blood sample is proportional to the amount of current generated during oxidization of the electron acceptor. Thus, it is possible to measure the concentration of blood sugar by measuring the amount of current through the lead terminal.

The structure and operation of an apparatus that is coupled to a biosensor strip having the above-mentioned configuration and measures sample reaction results will be described.

Figure 5:
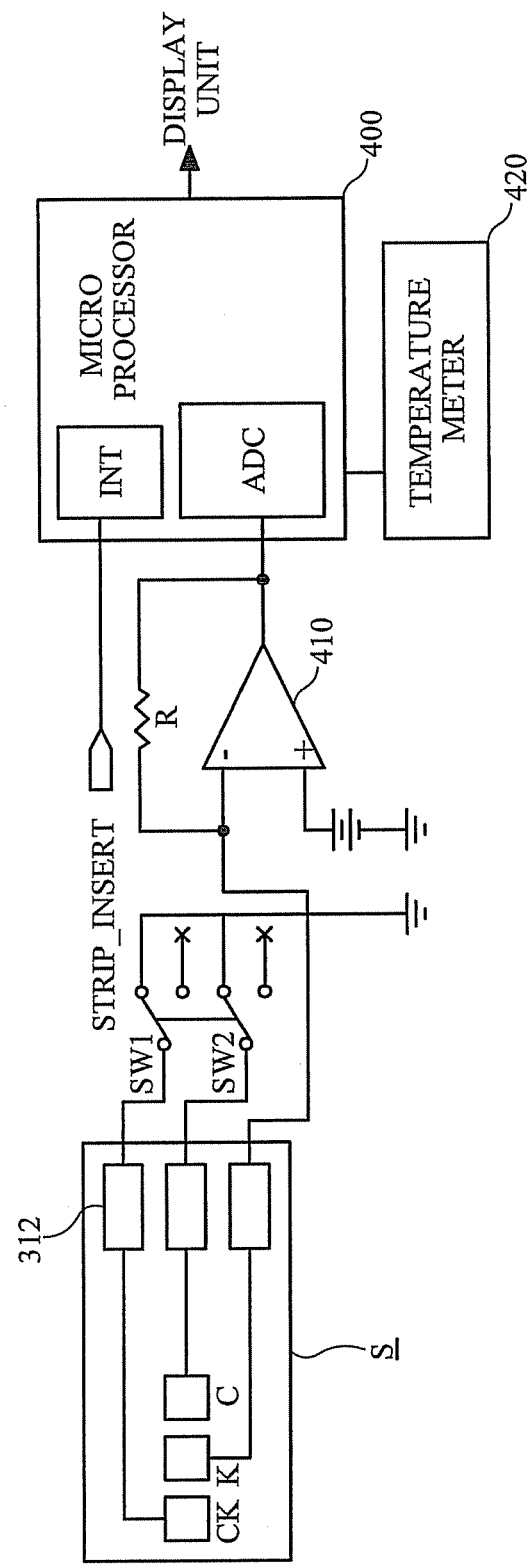
FIG. 5 is a circuit diagram of an apparatus for measuring sample reaction results on a biosensor according to an embodiment of the present invention.
Figure 6A:
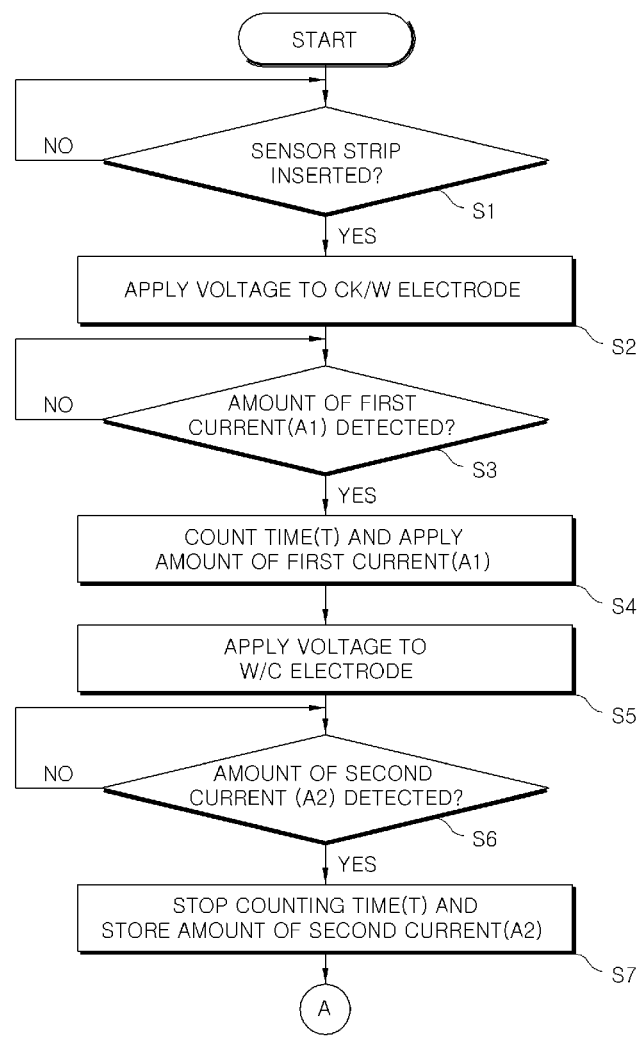
FIGS. 6A and 6B are flow charts of a method of measuring sample reaction results according to an embodiment of the present invention.
Figure 6B:
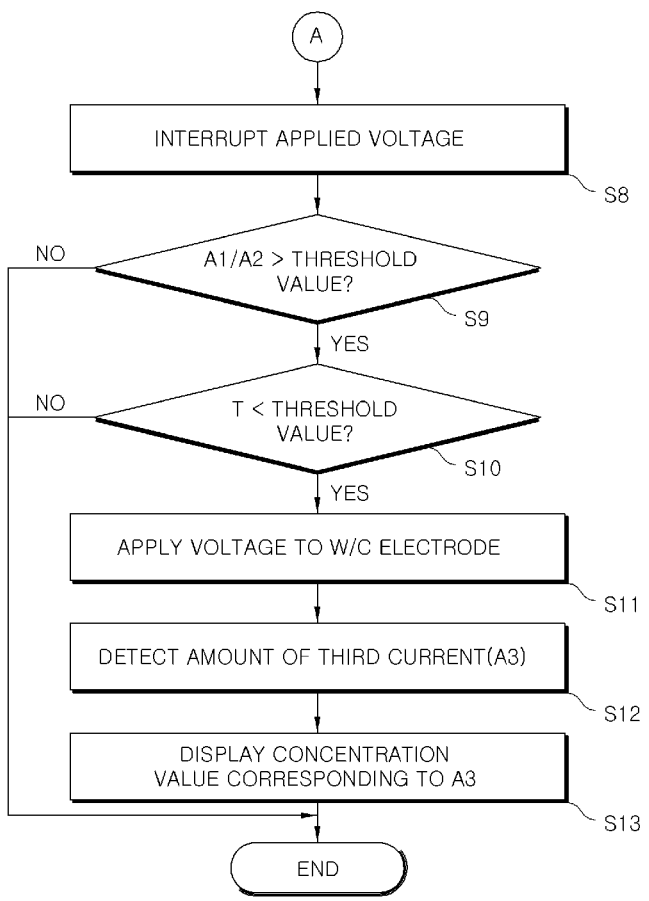

FIG. 5 is a circuit diagram of an apparatus for measuring sample reaction results on a biosensor according to an embodiment of the present invention. FIGS. 6A and 6B are flow charts of a method of measuring sample reaction results according to an embodiment of the present invention.

The apparatus for measuring sample reaction results on a biosensor S according to the present embodiment typically includes an amplifier 410, which is used as a current-voltage converter, switches SW1 and SW2, and a microprocessor 400. The apparatus may further include a temperature meter 420.

Each of the switches SW1 and SW2 is connected to electrodes, such as checking electrode CK and counter electrode C, of the biosensor S coupled to the apparatus to connect the electrodes CK and C to a ground terminal under control of the microprocessor 400.

A non-inverting terminal (+) of the amplifier 410 is connected to a voltage source that is grounded at its one end. An inverting terminal (−) of the amplifier 410 is connected to a working electrode W of the biosensor to detect the amount of current flowing through the working electrode. An example of the amplifier 410 is an operational amplifier.

The microprocessor 400 generally controls the apparatus for measuring sample reaction results on the biosensor. For instance, the microprocessor 400 controls the switches SW1 and SW2 so that voltage can be applied between the working electrode W and the checking electrode CK, and between the working electrode W and the counter electrode C when a biosensor strip S is coupled. The microprocessor 400 detects the amount of current flowing through the working electrode W and determines whether or not a sample is injected. The microprocessor 400 controls the switches SW1 and SW2 so that voltage can be applied between the working electrode W and the counter electrode C, detects the amount of current flowing through the working electrode W, and displays on a display unit a concentration value of a sample reaction result corresponding to the amount of detected current. For this, the microprocessor 400 includes a strip insert terminal to determine whether or not the biosensor strip is coupled. The microprocessor 400 further includes an analog-to-digital converter (ADC), which converts an output signal of the amplifier 410 to digital data, and an internal memory. The internal memory has a table storing concentration values of sample reaction results corresponding to the amount of detected current, or operation factors required for calculating the concentration values.

The temperature meter 420 detects and outputs temperature to the microprocessor 400. The microprocessor 400 compensates for the concentration values of sample reaction results based on temperature data.

The apparatus according to the present embodiment further includes a user interface having a display unit displaying the concentration values of sample reaction results, such as blood sugar level, and a plurality of key buttons.

The operation of the apparatus will be described in detail with reference to FIG. 6. In this case, it is assumed that blood is used as a sample to measure the concentration of blood sugar.

A sensor strip S is inserted into a strip slot of the apparatus. When an interrupt signal is generated upon insertion of the sensor strip S, the microprocessor 400 determines that the sensor strip S has been inserted (operation S1).

After the sensor strip S is inserted, the microprocessor 400 applies voltage to the checking electrode CK and the working electrode W in a sample reaction result detection mode (operation S2). At this time, the switch 1 SW1 is switched on to connect the checking electrode CK to a ground terminal.

After inserting the sensor strip S to the strip slot, blood is dropped on the bend 304 of the biosensor. The blood is moved by the insert hole 302 through the checking electrode CK to the working electrode W. When the blood reaches the working electrode W, current flows between the two electrodes CK and W by reaction on the enzyme reaction layer.

The current flowing through the working electrode W is converted to a voltage by a resistance R connected between the output terminal and inverting terminal (−) of the amplifier 410. The voltage is input to the microprocessor 400 and converted to digital data. Accordingly, the microprocessor 400 detects a voltage value converted to the digital data, i.e., the amount of first current A1 flowing through the working electrode W (operation S3).

After detecting the amount of first current A1 flowing through the working electrode W, the microprocessor 400 stores the amount of first current A1 and begins to count time T until the amount of second current A2 is detected (operation S4). The time T is used to determine whether or not there is an error in sample recognition.

Next, the microprocessor 400 applies voltage to the working electrode W and the counter electrode C (operation S5). To apply voltage to the working electrode W and the counter electrode C, the switch 1 SW1 and switch 2 SW2 are kept switched off and on, respectively. The voltage is applied to the working electrode W and the counter electrode C to check whether or not the sample is normally injected.

After applying voltage between the working electrode W and the counter electrode C, the microprocessor 40C detects the amount of second current A2 flowing through the working electrode W (operation S6). If the amount of second current A2 flowing through the working electrode W is detected, the microprocessor 400 stops counting the time T and temporarily stores the amount of second current A2 (operation S7). The voltage applied between the working electrode W and the counter C is interrupted (operation S8).

To determine whether or not there is an error in sample recognition, the microprocessor 400 compares the amount of first and second current A1 and A2 with a predetermined threshold value (operation S9). In this case, when the sample is uniformly injected over the entire surface of the electrode, the sample is determined to be normally injected.

If the amount of first and second current A1 and A2 is greater than the threshold value, the microprocessor 400 compares the time T with another threshold value (operation S10) to determine whether or not there is an error in sample recognition. If there is an error in sample injection, the time T is greater than the threshold value. Accordingly, it is further determined in operation S10 whether or not there is an error in sample recognition.

If there is not error in sample recognition through operations S9 and S10, the microprocessor 400 controls the switches 1 and 2 SW1 and SW2 so that voltage can be applied to the working electrode W and the counter electrode C (operation S11). Next, the microprocessor 400 detects the amount of third current A3 flowing through the working electrode W (operation S12), and acquires and displays a sample reaction result corresponding to the amount of third current A3, i.e., a blood sugar level, on a display unit (operation S13). The blood sugar level may be acquired from a memory storing blood sugar levels corresponding to the amount of detected current, or acquired by operating a predetermined factor to the amount of detected current. When the blood sugar level is directly computed, the blood sugar level may be compensated for with a value obtained from the temperature meter 420.

According to the present embodiment, it is determined whether or not a sample is normally injected, based on the amount of currents flowing through the working electrode by voltage applied between the working electrode and the checking electrode, and voltage between the working electrode and the counter electrode, and a time interval between times when the amount of currents is detected.

In addition, if the sample is determined to be normally injected, voltage is applied between the working electrode and the counter electrode and the amount of current is detected, thereby acquiring and displaying a concentration value of a reactive material in the sample. Accordingly, a user can check his or her own blood sugar level through the apparatus according to the present embodiment.

As apparent from the above description, it is determined whether or not a sample is normally injected, based on the amount of currents flowing through a working electrode by voltages applied between the working electrode and each of electrodes, and a time interval between times when the amount of currents is detected.

In addition, if the sample is determined to be normally injected, voltage is applied between the working electrode and any one of the electrodes and the amount of current is detected, thereby acquiring and displaying a concentration value of a reactive material in the sample.

While the present invention has been described with reference to exemplary embodiments thereof, it will be understood by those skilled in the art that various changes in form and details may be made therein without departing from the scope of the present invention as defined by the following claims.

What is claimed is:

1. An apparatus for measuring a sample reaction result on a biosensor having a working electrode, a counter electrode, and a checking electrode, the apparatus comprising:
   switches configured to selectively connect each of the counter electrode and the checking electrode to a ground terminal;
   an amplifier configured to be connected at one terminal to a voltage source and at another terminal to the working electrode of the biosensor, so as to detect an amount of current flowing through the working electrode; and
   a microprocessor programmed to:
   control the switches so that a voltage can be applied between the working electrode and the checking electrode upon coupling of a sensor strip,
   detect an amount of first current flowing through the working electrode and checking electrode,
   control the switches so that a voltage can be applied between the working electrode and the counter electrode,
   detect an amount of second current flowing through the working electrode and counter electrode,
   determine whether or not a sample is properly injected by comparing the detected amounts of the first and second currents and a time interval between times when the first and second currents are detected with predetermined threshold values,
   if it is determined that the sample is properly injected, apply a voltage between the working electrode and the counter electrode and detect an amount of third current flowing through the working electrode, and
   acquire and display a concentration value as a sample reaction result corresponding to the detected amount of third current on a display unit.

2. The apparatus of claim 1, wherein the microprocessor includes a memory configured to store concentration values as sample reaction results corresponding to the detected amount of third current.

3. The apparatus of claim 1, wherein the microprocessor applies the detected amount of third current to a predetermined factor to acquire the concentration value as the sample reaction result.

4. The apparatus of claim 1, wherein the microprocessor indicates a sample recognition error if the detected amounts of first and second current and the time interval fail to meet predetermined conditions.

5. The apparatus of claim 2, wherein the microprocessor indicates a sample recognition error if the detected amounts of first and second current and the time interval fail to meet predetermined conditions.

6. The apparatus of claim 3, wherein the microprocessor indicates a sample recognition error if the detected amounts of first and second current and the time interval a time interval fail to meet predetermined conditions.

7. An apparatus for measuring a sample reaction result on a biosensor having a working electrode, a checking electrode and a counter electrode, the apparatus comprising a microcontroller programmed to:
   apply a voltage between the checking electrode and the working electrode;
   detect a first current flowing between the checking electrode and the working electrode after a sample is injected into a sample receiving region;
   apply a voltage between the counter electrode and the working electrode;
   detect a second current flowing between the counter electrode and the working electrode;
   measure a time interval from the time the first current is detected to the time the second current is detected;
   compare the first and second currents with a predetermined threshold current value and the time interval with a predetermined time value;
   re-apply a voltage between the counter electrode and the working electrode if the first and second currents are more than the predetermined threshold current value and the time interval is shorter than the predetermined time value;
   measure a third current between the counter electrode and the working electrode; and
   compute a concentration value corresponding to the third current as the sample reaction result.

8. The apparatus of claim 7, wherein the microcontroller is further programmed to display an error message if the time interval is longer than the predetermined time value.

9. The apparatus of claim 7, wherein the microcontroller is further programmed to display an error message if either of the first and second currents is less than the predetermined threshold current value.

10. An apparatus for measuring a sample reaction result on a biosensor having a working electrode, a checking electrode and a counter electrode, the apparatus comprising a microcontroller programmed to:
    apply a voltage between the checking electrode and the working electrode and between the counter electrode and the working electrode;
    detect amounts of currents flowing through the working electrode and detect a time interval between times when the amounts of currents are detected; and
    determine whether or not a sample is properly injected by comparing the amounts of detected currents and the detected time interval with predetermined threshold values;
    if it is determined that the sample is properly injected, apply a voltage between the working electrode and the counter electrode;
    re-detect an amount of current flowing through the working electrode; and
    compute a concentration value as a sample reaction result corresponding to the amount of the re-detected current.

* * * * *